(12) United States Patent
Ellegård et al.

(10) Patent No.: US 11,180,723 B2
(45) Date of Patent: Nov. 23, 2021

(54) VERTICAL PLUG-FLOW PROCESS FOR SIMULTANEOUS PRODUCTION OF ETHANOL AND A FERMENTED, SOLID TRANSFORMATION PRODUCT OF THE SUBSTRATE

(71) Applicant: Hamlet Protein A/S, Horsens (DK)

(72) Inventors: Katrine Hvid Ellegård, Ry (DK); Jonatan Ahrens Dickow, Stouby (DK); Stig Victor Petersen, Beder (DK); Laila Thirup, Skanderborg (DK); Svend Andreas Geleff, Rødding (DK)

(73) Assignee: HAMLET PROTEIN A/S, Horsens (DK)

( * ) Notice: Subject to any disclaimer, the term of this patent is extended or adjusted under 35 U.S.C. 154(b) by 9 days.

(21) Appl. No.: 16/315,146

(22) PCT Filed: Jun. 27, 2017

(86) PCT No.: PCT/EP2017/065781
§ 371 (c)(1),
(2) Date: Jan. 3, 2019

(87) PCT Pub. No.: WO2018/007196
PCT Pub. Date: Jan. 11, 2018

(65) Prior Publication Data
US 2019/0309244 A1 Oct. 10, 2019

Related U.S. Application Data (63) Continuation of application No. PCT/EP2017/065781, filed on Jun. 27, 2017.

(30) Foreign Application Priority Data

Jul. 6, 2016 (EP) .................................. 16178170

(51) Int. Cl.
| | |
|---|---|
| *C12M 1/00* | (2006.01) |
| *C12M 1/34* | (2006.01) |
| *C12N 1/18* | (2006.01) |
| *A61K 36/31* | (2006.01) |
| *A23K 10/12* | (2016.01) |
| *A61K 36/48* | (2006.01) |
| *A23J 3/14* | (2006.01) |
| *A23K 10/38* | (2016.01) |

(Continued)

(52) U.S. Cl.
CPC .............. *C12M 21/12* (2013.01); *A23J 3/14* (2013.01); *A23K 10/12* (2016.05); *A23K 10/38* (2016.05); *A23L 33/185* (2016.08); *A61K 36/28* (2013.01); *A61K 36/31* (2013.01); *A61K 36/48* (2013.01); *C12M 23/02* (2013.01); *C12M 23/20* (2013.01); *C12M 23/38* (2013.01); *C12M 41/12* (2013.01); *C12M 41/36* (2013.01); *C12M 45/06* (2013.01); *C12M 47/10* (2013.01); *C12M 47/14* (2013.01); *C12N 1/18* (2013.01); *C12P 1/02* (2013.01); *C12P 7/10* (2013.01); *A61K 2236/00* (2013.01); *C12P 2201/00* (2013.01); *C12P 2203/00* (2013.01); *Y02E 50/10* (2013.01); *Y02P 60/87* (2015.11)

(58) Field of Classification Search
None
See application file for complete search history.

(56) References Cited

U.S. PATENT DOCUMENTS 4,409,329 A * 10/1983 Silver ................. C12P 7/10
435/105
4,735,724 A 4/1988 Chynoweth et al.
(Continued)

FOREIGN PATENT DOCUMENTS

| EP | 2453004 A1 | 5/2012 |
|---|---|---|
| JP | 2003-047456 | 2/2003 |

(Continued)

OTHER PUBLICATIONS

W.J.B. van den Bergh et al. "Computer simulation model of a Nauta mixer". Powder Technology, 1993, vol. 77, pp. 19-30.*
Lopez-Linares et al. "Bioethanol production from rapeseed straw at high solids loading with different process configurations". Fuel. 2014, 122, pp. 112-118.*
Tisseyre et al., "Conception and Characterization of a Continuous Plug Flow Bioreactor," Bioprocessing Engineering, vol. 13, No. 3, pp. 113-118 (Jan. 1995), XP008066218.
(Continued)

*Primary Examiner* — Vera Afremova
(74) *Attorney, Agent, or Firm* — Foley & Lardner LLP (57) ABSTRACT

The invention relates to a method for the simultaneous production of a solid transformation product of the substrate and crude ethanol comprising the following steps: •preparing a substrate from milled or flaked biomass comprising proteinaceous matter which originates from soya bean, rape seed, or mixtures thereof, optionally in further mixture with proteinaceous matter originating from fava beans, peas, sunflower seeds, lupine, cereals, and/or grasses, •mixing said substrate with live yeast in a dry matter ratio of from 1:1 to 10,000:1 and adding water in an amount which provides a ratio of wet bulk density to dry bulk density from 0.60 to 1.45 in the resulting mixture; •incubating said mixture for 1-48 hours at a temperature of about 20-60° C.; and •separating crude ethanol and wet solid transformation product from said mixture; further comprising that the incubation is performed as a continuous plug-flow process in a vertical, non-agitated, closed incubation tank with inlet means for said mixture and additives and outlet means for the solid transformation product and crude ethanol. The invention further relates to the products of this method as well as uses thereof.

31 Claims, 3 Drawing Sheets

(51) Int. Cl.
*C12P 7/10* (2006.01)
*A23L 33/185* (2016.01)
*A61K 36/28* (2006.01)
*C12P 1/02* (2006.01)

(56) References Cited

U.S. PATENT DOCUMENTS

| | | | |
|---|---|---|---|
| 8,153,174 | B2 | 4/2012 | Hansen |
| 9,416,377 | B2 * | 8/2016 | Abbas .................. C12P 19/14 |
| 9,528,128 | B2 | 12/2016 | Hansen et al. |
| 10,047,379 | B2 | 8/2018 | Hansen et al. |
| 2006/0292677 | A1 | 12/2006 | Ostrander |
| 2016/0076067 | A1 | 3/2016 | Cotti Comettini et al. |
| 2019/0002929 | A1 | 1/2019 | Hansen et al. |

FOREIGN PATENT DOCUMENTS

| | | |
|---|---|---|
| JP | 2007-000144 | 1/2007 |
| JP | 2011-516095 A | 5/2011 |
| JP | 2014-530600 A | 11/2014 |
| WO | WO-2006/102907 A1 | 10/2006 |
| WO | WO-2009/129320 A2 | 10/2009 |
| WO | WO-2013/050456 A1 | 4/2013 |

OTHER PUBLICATIONS

U.S. Appl. No. 16/955,315, filed Jun. 18, 2020, Dickow et al.
U.S. Appl. No. 16/955,328, filed Jun. 18, 2020, Thirup et al.

* cited by examiner

Fig. 3 Density Ratios vs. Moisture for Soy- (SBM) and Rape Seed Meal (RSM) and Mixtures

VERTICAL PLUG-FLOW PROCESS FOR SIMULTANEOUS PRODUCTION OF ETHANOL AND A FERMENTED, SOLID TRANSFORMATION PRODUCT OF THE SUBSTRATE

CROSS-REFERENCE TO RELATED APPLICATIONS

The present application is the U.S. National Stage of International Application PCT/EP2017/065781, filed Jun. 27, 2017, and claims priority to European Patent Application No. 16178170.3, filed Jul. 6, 2016.

FIELD OF THE INVENTION

The present invention relates to a solid substrate incubation method for the simultaneous production of a valuable solid transformation product of the substrate and crude ethanol by a continuous plug flow process in a vertical, non-agitated, closed tank where the transport is mediated by gravitational force.

Furthermore, it relates to the products obtainable by the method as well as their use.

BACKGROUND OF THE INVENTION

There is a need for bio-products that primarily can be used as food or feed or as ingredients in food or feed. The basic constituents in such products are proteins, fats, and carbohydrates. Suitable biomasses for such products are oil bearing crops such as oilseeds, cereals, and legumes. Cereals have a protein content up to 15% e.g. in wheat, and legumes have a protein content of up to 40% e.g. in soya beans, based on dry matter.

A general problem especially related to pulses and fruits and seeds from legumes are the content of indigestible oligosaccharides, such as stachyose and raffinose, causing flatulence and diarrhea when fermented in the colon.

There is a similar need for the development of sustainable energy sources, and bio ethanol is an attractive source as fuel for e.g. transportation. Therefore, there is a need for a process that can produce bio ethanol at a low cost.

Low cost methods known in the art are solid substrate or solid-state fermentation (SSF) processes performed with low water content. The process consists of a solid, moist substrate inoculated with suitable microorganisms and left for fermentation under temperature controlled conditions for a period of time.

Normally the substrate is incubated batch wise on flatbeds without stirring; one example of this process is known as the Koji process. Batch processes are also performed using stirring means.

Continuous SSF processes are also described in literature using the following bioreactors: Stirred tank, rotating drum and tubular flow reactors. One example of a tubular flow reactor is the screw conveyor type.

WO 2006/102907 A1, incorporated herein as reference, discloses a method of preparing a protein product derived from yeast and proteinaceous pulse parts by incubating under anaerobic conditions at a water content not exceeding 80% followed by incubation in a closed system.

WO2013050456, incorporated herein as reference, discloses a method for the simultaneous production of crude ethanol and a solid product. The production is performed in one or more interconnected screw conveyers as a batch process or a continuous process.

U.S. Pat. No. 4,735,724 discloses a non-mixed vertical tower anaerobic digester and a process for digestion of the biodegradable part of feedstock by methane producing microorganisms. The method is characterized in that there is a withdrawal of liquid from a middle or lower zone to the top of the tower.

EP 2 453 004 B1 discloses a method for anaerobic fermentation of organic material in a closed tank and top down feed in the tank under the action of the gravity. The method is characterized in that the fermenting mass is agitated by alternately increasing the pressure of the product gas and abruptly relieving the pressure of the product gas.

The object of the present invention is to provide an alternative method for the production of crude bio ethanol and the simultaneous production of a valuable solid transformation product.

Another object is to provide a method, which can be performed in a larger but simpler reactor design than the prior art design.

Yet an object is to provide an alternative method for treatment of biomasses based on mixtures of biomasses, in particular soya bean or rape seed or mixtures thereof.

These objects are fulfilled with the method of the present invention.

SUMMARY OF THE INVENTION

Accordingly, in one aspect of the present invention it relates to a method for the simultaneous production of a solid transformation product of the substrate and crude ethanol comprising the following steps:
preparing a substrate from milled or flaked biomass comprising proteinaceous matter which originates from soya bean, rape seed, or mixtures thereof, optionally in further mixture with proteinaceous matter originating from fava beans, peas, sunflower seeds, lupine, cereals, and/or grasses,
mixing said substrate with live yeast in a dry matter ratio of from 1:1 to 10,000:1 and adding water in an amount which provides a ratio of wet bulk density to dry bulk density from 0.60 to 1.45 in the resulting mixture;
incubating said mixture for 1-48 hours at a temperature of about 20-60° C.; and
separating crude ethanol and wet solid transformation product from said mixture;
further comprising that said incubation is performed as a continuous plug-flow process in a vertical, non-agitated, closed tank with inlet means for said mixture and additives and outlet means for said solid transformation product and crude ethanol.

The present method for treatment of biomass uses gravitational force to transport/move the biomass during incubation. Although the use of gravity for transportation in general is straightforward, it requires careful selection of reaction conditions for the specific purpose, such as in the case of the present plug-flow process.

Normally, when the water content is increased, an incubation mixture tends to compact, by the reduction of void volume, so that the transportation behavior is affected negatively. When a certain water content is reached the mixture is compacted to an extent so that the transportation by gravitational force is stopped. The material will stick to the walls of the reactor, and the uniform plug-flow is disrupted resulting in uneven retention time of the biomass.

Furthermore, if the incubation is performed at elevated pressure, which may be the case under the gravity effect, the reaction:

tends to slow down.

The solution according to the present invention to the problem connected with transportation by gravitational force of the incubation mixture is to make use of a closed tank as defined in the claims for incubation wherein the flow of material can be kept so high and uniform that plug-flow conditions are achieved and maintained. The speed of flow is regulated by the inlet and outlet means and by the dimensions (width to height ratio) of the tank.

Furthermore, the solution according to the invention must secure balancing of the water content in the incubation mixture so that the water activity on the particle surface is sufficient for the reaction process. This is achieved by keeping the ratio wet bulk density to dry bulk density of the substrate low and within certain limits as defined in claim 1. Under these conditions the mixture acts as a free-flowing powder.

More specifically, the present inventors have found that the necessary uniform process can be achieved by using a substrate/biomass having a ratio of wet bulk density to dry bulk density from 0.60 to 1.45. In combination with the present vertical design for the plug-flow process it is possible to secure a uniform plug-flow and ensure the same processing time for the transformation product. Finally, the method of the present invention is conducted without agitation. This is contrary to the prior art methods of industrial ethanol production which require agitation from a mixer to keep the applied organism suspended.

The vertical design is less expensive in investment than a horizontal design due to its larger capacity in a single production line. It is also less expensive to maintain due to less mechanical movements. The use of a non-agitated tank further contributes to reduced operational costs.

By this method more than 98% by weight of the crude ethanol produced can be recovered. The yield of ethanol is dependent upon the content of carbohydrates in the substrate mixture and the conversion into fermentable sugars. On the basis on defatted soya, it is possible to generate 4-5% by weight of ethanol, whereas on wheat approx. 20% by weight can be obtained.

The invention in a second aspect provides a crude ethanol obtainable by a method according to the invention and further comprising small amounts of impurities resulting from the incubation of said biomass with said yeast, e.g. other alcohols and ethers.

In a third aspect the invention provides a solid transformation product of the substrate obtainable by a method according to the invention comprising proteins in an amount of about 25-90% by weight on dry matter basis, and optionally glyceride in an amount of about 0.05-30% by weight on dry matter basis.

The invention in a $4^{th}$ aspect provides the use of a solid transformation product of the invention for human and/or animal consumption or as an ingredient to be used in a food or feed product or as an ingredient of a cosmetic or a pharmaceutical product or a nutritional supplement.

In a $5^{th}$ aspect the invention provides a food, feed, cosmetic or pharmaceutical product or a nutritional supplement containing from 1% to 99% by weight of a solid transformation product according to the invention.

Definitions

In the context of the current invention, the following terms are meant to comprise the following, unless defined elsewhere in the description.

The terms "about", "around", "approximately", or "~" are meant to indicate e.g. the measuring uncertainty commonly experienced in the art, which can be in the order of magnitude of e.g. +/−1, 2, 5, 10, 20, or even 50%.

The term "comprising" is to be interpreted as specifying the presence of the stated part(s), step(s), feature(s), composition(s), chemical(s), or component(s), but does not exclude the presence of one or more additional parts, steps, features, compositions, chemicals or components. E.g., a composition comprising a chemical compound may thus comprise additional chemical compounds, etc.

Plug-Flow Process:

In this type of continuous process, the reaction mixture flows through e.g. a tubular or polyhedral reactor with limited back mixing. The flow is a laminar flow where the composition of the reaction mixture changes along the axial direction of the reactor, or a uniform mass flow.

Biomass:

Comprises biological material, as produced by the photosynthesis and that can be used as raw material in industrial production. In this context, biomass refers to plant matter in the form of seeds, cereals, pulses, grasses, e.g. beans and peas, etc., and mixtures thereof, and in particular fruits and seeds of legumes. Furthermore, a biomass comprising pulses is specifically applicable due to the protein content and composition.

Incubation:

Is the process to incubate cultures of microorganisms on a substrate for a specific purpose, e.g. incubating yeast on a carbohydrate to produce alcohol.

Solid Transformation Product of the Substrate:

In general treatment of biomass by incubation with microorganisms can be divided into four types:

Production of biomass—cellular material

Production of extracellular components—chemical compounds, metabolites, enzymes

Production of intracellular components—enzymes, etc.

Transformation product of the substrate—the transformed substrate is the product In the present context, solid transformation product of the substrate refers to a product resulting from incubation of the selected biomass with live yeast and optionally enzymes.

Bulk Density:

The density of a powder is determined by placing a fixed volume of the powder in a measuring cup and determining the weight or by determining the weight of a measured volume of a powder. By this test the following features can be determined:

Bulk density (also known as pour density)=mass/untapped dry volume in g/mL or kg/m$^3$;

Wet bulk density (also known as total density)=the ratio of the total mass ($M_s$+$M_l$) to its total volume;

$M_s$=mass of solids and $M_l$=mass of liquids.

Normally, the bulk density is determined in accordance with International Standards ISO 697 and ISO 60, but due to the nature of the substances this was not applicable in the present context. The individual method used is described in the examples.

Oligosaccharides and Polysaccharides:

An oligosaccharide is a saccharide polymer containing at least two component monomer sugars. Polysaccharides are saccharide polymers containing many component monomer sugars, also known as complex carbohydrates. Examples include storage polysaccharides such as starch and structural polysaccharides such as cellulose.

Carbohydrates:

Comprise mono-, di-, oligo- and polysaccharides.

Proteinaceous Materials:

Comprise organic compounds with a substantial content of proteins made of amino acids arranged in one or more chains. At a chain length of up to approximately 50 amino acids the compound is called a peptide; at higher molecular weight the organic compound is called a polypeptide or a protein.

Fats:

Comprise esters between fatty acids and glycerol. One molecule of glycerol can be esterified to one, two and tree fatty acid molecules resulting in a monoglyceride, a diglyceride or a triglyceride respectively. Usually fats consist of mainly triglycerides and minor amounts of lecithins, sterols, etc. If the fat is liquid at room temperature it is normally called oil. With respect to oils, fats, and related products in this context, reference is made to "Physical and Chemical Characteristics of Oils, Fats and Waxes", AOCS, 1996, as well as "Lipid Glossary 2", F. D. Gunstone, The Oily Press, 2004.

Glycerides:

Comprise mono-, di-, and triglycerides.

Processing Aids:

1. Enzymes

Enzyme(s) is a very large class of protein substances with the ability to act as catalysts. Commonly, they are divided in six classes, and the main classes falling within the scope of this invention can be transferases that transfer functional groups or hydrolases that hydrolyze various bonds. Typical examples can comprise: protease(s), peptidase(s), ($\alpha$-)galactosidase(s), amylase(s), glucanase(s), pectinase(s), hemicellulase(s), phytase(s), lipase(s), phospholipase(s), transferase(s), and oxido-reductase(s).

2. Plant Components and Organic Processing Agents

Some of the functional properties that are important in this context are: Antioxidant, anti-bacterial action, wetting properties and stimulation of enzyme activity.

The list of plant-based components is huge, but the most important are the following: Rosemary, thyme, oregano, flavonoids, phenolic acids, saponins, and $\alpha$- and $\beta$-acids from hops e.g. $\alpha$-lupulic acid for the modulation of soluble carbohydrates.

Furthermore, organic acids e.g. sorbic-, propionic-, lactic-, citric-, and ascorbic acid, and their salts for the adjustment of the pH-value, preservation and chelating properties is part of this group of processing aids.

3. Inorganic Processing Agents

Comprise inorganic compositions that can preserve against bacterial attack during processing e.g. sodium bisulfite, etc. Anticaking and flow improving agents in the final product e.g. potassium aluminum silicate, etc.

Comprise inorganic acids e.g. hydrochloric acid.

Processed Food Products:

Comprise dairy products, processed meat products, sweets, desserts, ice cream desserts, canned products, freeze dried meals, dressings, soups, convenience food, bread, cakes, etc.

Processed Feed Products:

Comprise ready-to-use feed for animals such as piglets, calves, poultry, furred animals, sheep, cats, dogs, fish, and crustaceans, etc.

Pharmaceutical Products:

Comprise products, typically in the form of a tablet or in granulated form, containing one or more biologically active ingredients intended for curing and/or alleviating the symptoms of a disease or a condition. Pharmaceutical products furthermore comprise pharmaceutically acceptable excipients and/or carriers. The solid bio products herein disclosed are very well suited for use as a pharmaceutically acceptable ingredient in a tablet or granulate.

Cosmetic Products:

Comprise products intended for personal hygiene as well as improved appearance such as conditioners and bath preparations.

DETAILED DESCRIPTION OF THE INVENTION

In a first embodiment of the method of the invention at least 20% by weight of the biomass, such as at least 30%, at least 40%, at least 50%, at least 60%, at least 70%, at least 80%, or at least 90% by weight, comprises proteinaceous matter originating from defatted soya flakes. The soya flakes may also be dehulled.

In a second embodiment of the method of the invention at least 20% by weight of the biomass, such as at least 30%, at least 40%, at least 50%, at least 60%, at least 70%, at least 80%, or at least 90% by weight, comprises proteinaceous matter originating from defatted rape seeds.

In a third embodiment of the method of the invention the biomass comprises proteinaceous matter originating from defatted soya flakes in an amount of from 5% to 95% by weight in mixture with proteinaceous matter originating from defatted rape seed in an amount of from 95% to 5% by weight optionally in further mixture with proteinaceous matter originating from fava beans, peas, sunflower seeds and/or cereals in amounts to make up a total amount of the proteinaceous matter of 100% by weight.

In any of the embodiments of the invention the biomass comprising proteinaceous matter may further comprise oligosaccharides and/or polysaccharides and/or further comprises oils and fats, e.g. from seeds of oil bearing plants.

In any of the embodiments of the invention the solid transformation product of the substrate may be a product of the transformation of proteinaceous matter, oligosaccharides and/or polysaccharides originating from said biomass, such as a transformation product of pulses, such as soya, pea, lupine, sunflower, and/or cereals, such as wheat, or maize, or from seeds of oil bearing plants, e.g. rape seed.

In any of the above embodiments the dry matter ratio of biomass to live yeast is from about 1:1 to about 10000:1, such as from about 2:1 to about 8000, e.g. 3:1, 5:1, 10:1, 15:1, 20:1, 30:1, 50:1, 70:1, 75:1, 85:1, 100:1, 200:1, 300:1, 500:1, 1000:1, 2000:1, 3000:1, 4000:1, 5000:1, or 7000:1.

In any of the embodiments of the invention water is added to the substrate in an amount to provide a ratio of wet bulk density to dry bulk density from about 0.60 to 1.45 in the substrate, such as from about 0.65 to about 1.40, e.g. 0.70, 0.75, 0.80, 0.85, 0.90, 0.95, 1.00, 1.10, 1.15, 1.20, 1.25, 1.30, or 1.35.

In any of the embodiments of the invention at least 40% by weight of the biomass, such as at least 50%, at least 60%, at least 70%, at least 80% or at least 90% by weight, may comprise proteinaceous matter originating from defatted rape seeds, whereas water may be added to the substrate in an amount to provide a ratio of wet bulk density to dry bulk density from about 0.65 to about 1.10, such as 0.75, 0.80, 0.85, 0.90, 0.95, 1.00, or 1.05.

In any of the embodiments of the invention said yeast may be selected among *Saccharomyces cerevisiae* strains, including spent brewer's yeast and spent distiller's yeast and spent yeast from wine production, baker's yeast, as well as yeast strains fermenting C5 sugars.

In any of the embodiments of the invention one or more processing aids selected from enzymes, plant components and organic and inorganic processing agents may be added to the substrate before or during incubation.

In any of the embodiments of the invention the filling degree of said closed incubation tank may be kept constant. This will result in a uniform flow.

In any of the embodiments of the invention α-galactosidase may be added to the substrate before or during incubation, e.g. an α-galactosidase preparation having an activity of about 5,000 α-galactosidase units pr. g. of enzyme product is added in an amount of from about 0.001% to about 1% by weight of the dry matter of the substrate, such as an amount of 0.005%, 0.01%, 0.015%, 0.02%, 0.03%, 0.05%, 0.1%, 0.5%, or 0.75% by weight.

In any of the embodiments of the invention the incubation can be carried out under anaerobic conditions. The anaerobic conditions are facilitated by the present invention.

In any of the embodiments of the invention the water content in the incubation mixture may be from 35% to 70% by weight, such as 40%, 45%, 50%, 55%, 60%, or 65% by weight. Thus, the water content in the initial mixture normally does not exceed 70% by weight and it may vary from e.g. from 40% to 65%, from 45% to 60%, from 48% to 52%, or 50% to 55%, such as 49, 50, 51, 52, 53, or 54%.

In any of the embodiments of the invention the mixture is incubated for 1-48 hours at 20-60° C., e.g. for 1-42 hours at 20-60° C. or 25-60° C. or 30-50° C. or 30-40° C., or for 2-36 hours at one of the here mentioned temperature intervals, or for 3-24 hours at one of the here mentioned temperature intervals, or for 5-18 hours at one of the here mentioned temperature intervals, or for 8-15 hours at one of the here mentioned temperature intervals, or for 10-12 hours at one of the here mentioned temperature intervals.

In any of the embodiments of the invention the solid transformation product of the substrate may by dried, optionally followed by milling.

In any of the embodiments of the invention the substrate mixture may be incubated at a time and a temperature sufficient to inactivate the yeast, anti-nutritional factors and the enzyme(s) if used partly or totally, and if desired. Generally, a higher temperature is applied for a shorter period, whereas a lower temperature is applied for a longer time to inactivate the live yeast, the anti-nutritional factors and the enzymes.

In any of the embodiments of the invention the non-agitated, closed incubation tank can be of a vertical, oblong cylindrical or polyhedral type. The advantage of using this type is that it is space-saving and as it is non-agitated the operating costs and maintenance costs for mixing equipment are avoided.

In any of the embodiments of the invention the area in the upper part of said non-agitated, closed incubation tank may be less than the area in the lower part i.e. the tank is of conical shape. The advantage of this is that the slip effect is increased so that biomasses with a reduced flowability can be used.

In any of the embodiments of the invention the non-agitated, closed incubation tank may have insulating matting or a thermal dimple jacket and means to control the temperature inside the incubation tank.

By the present method the ethanol can be separated from the substrate mixture by conventional methods, such as vacuum and/or injection of steam, and more than 98% by weight of the crude ethanol produced may be recovered. The yield of ethanol is dependent upon the content of carbohydrates in the incubation mixture and the conversion into fermentable sugars. Based on defatted soya it is possible to generate 4-5% by weight of ethanol, whereas on wheat approx. 20% by weight can be obtained.

Thus, the invention in its second aspect provides a crude ethanol obtainable by a method according to the invention and further comprising small amounts of by-products resulting from the incubation of said biomass, e.g. other alcohols and ethers.

In a first embodiment of the solid transformation product of the substrate of the invention it has been dried to a water content of not more than 15%, 13%, 10%, 6%, 4%, or 2% by weight and is optionally being in milled form.

In any embodiments of the solid product of the invention it can be a product of the transformation of proteinaceous matter, oligosaccharides and/or polysaccharides originating from said biomass. The solid transformation product will have reduced content of anti-nutritional factors, such as trypsin inhibitors, antigens, flatulence-producing oligosaccharides, e.g. stachyose and raffinose; phytic acid, and lecithins.

In any of the embodiments of the solid product of the invention it may comprise at least 40% proteinaceous matter by weight of dry matter originating from soya.

In any of the embodiments of the solid product of the invention it may comprise at least 40% proteinaceous matter by weight of dry matter originating from rape seed.

In any of the embodiments of the solid product of the invention it may comprise proteins in an amount of 30-65% by weight on dry matter basis originating from plant parts of soya, rape seed, or sun flower, or mixtures thereof.

In any of the embodiments of the solid product of the invention it may comprise a total amount of raffinose, stachyose, and verbascose of 3% by weight or less, such as 2% or less, 1% or less, 0.5% or less, or 0.4% or less.

In any of the embodiments of the solid product of the invention is may comprise organic acids selected from succinic acid, acetic acid, and mixtures thereof in amounts of 0.01% to 0.5% by weight.

Finally, the invention relates to a food, feed, cosmetic or pharmaceutical product or a nutritional supplement containing from 1% to 99% by weight of a solid transformation product according to the invention.

EXAMPLES

Example 1

Comparative Incubation in an Open and a Closed Batch Tank of a Biomass Comprising Polysaccharides and Proteins from Pulses In the following the incubation at atmospheric pressure and elevated pressure of a biomass based on soya is compared.

1.1 Substrate Mixture:

10 kg of dehulled, defatted and desolventised soya flakes were mixed with 3 kg of a slurry of yeast (10% dry matter) and added water in an amount to reach a dry matter content of 51% by weight in the mixture. The ratio wet bulk density/dry bulk density of the substrate mixture was 0.832.

1.2 Incubation Tank:

A 40-litre insulated autoclave equipped with a temperature- and pressure gauge probe was used as an open and closed batch tank.

The tank was filled with approx. 15 kg of substrate mixture and left open for the test at atmospheric pressure, and when closed for the incubation under pressure the lid had a valve with a pressure regulator set to open at 6.0 bar.

Figure 1:
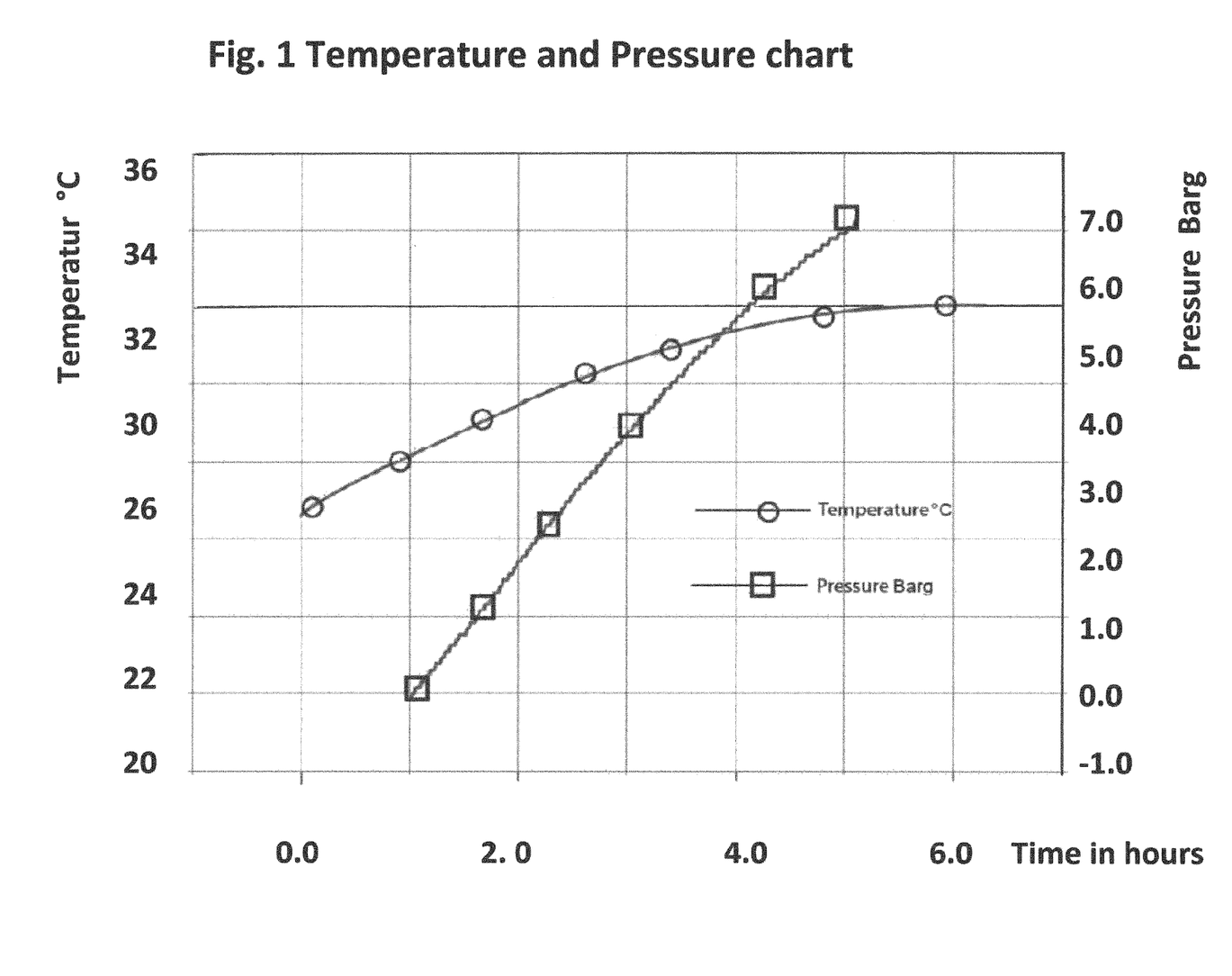
FIG. 1 illustrates the temperature and pressure increase as a function of incubation time.

1.3 Results:

FIG. 1 illustrates the temperature and pressure increase as a function of incubation time.

Figure 2:
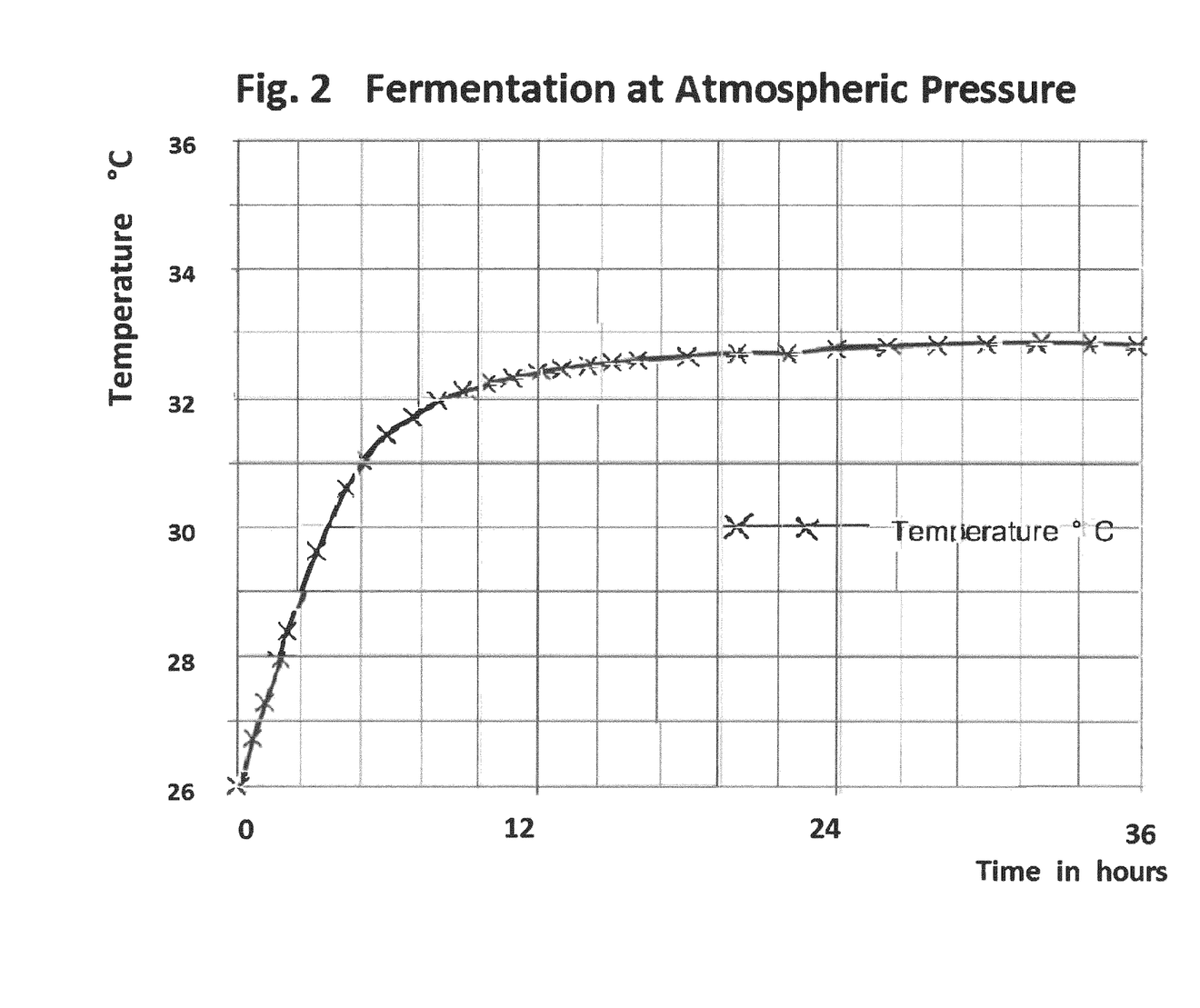
FIG. 2 illustrates the temperature development during the test fermentation at atmospheric pressure as a function of incubation time.

FIG. 2 illustrates the temperature development during the test at atmospheric pressure as a function of incubation time.

The reduction of oligosaccharides after 6 hours of incubation is tabulated in the following:

| Parameter | Stachyose In % by weight | Raffinose In % by weight |
|---|---|---|
| Substrate mixture | 4.0 | 1.5 |
| Incubation at elevated pressure | 1.5 | 0.0 |
| Incubation at atmospheric pressure | 1.6 | 0.0 |

From the results it can be deducted, that it is possible to incubate under pressure, and at the same time get a reduction of the oligosaccharide content similar to what can be obtained at atmospheric pressure by choosing at the right moisture conditions i.e. the ratio wet bulk density/dry bulk density.

Example 2

Ratio of Wet Bulk Density/Dry Bulk Density for Preferred Substrates Based on Various Biomasses 2.1 Biomasses Used in the Examination:

Soya

The soya used was defatted soya bean meal.

Maize

The maize used was whole maize, ground on a hammer mill through a 3.5 mm sieve.

Wheat

The wheat used was whole wheat, ground on a hammer mill through a 3.5 mm sieve.

Sunflower

The sunflower used was defatted sunflower pellets, ground in a blender.

Rapeseed

The rapeseed used was defatted rapeseed meal.

Fava Beans

The beans used were whole fava beans, ground in a blender.

Pea Protein

The pea protein used was a pea protein concentrate.

2.2 Description of the Procedure:

The amount(s) of biomass and water tabulated in the following was mixed for ten minutes followed by fifty minutes of equilibration in a closed container.

After this the material was poured into a measuring cup of 500 mL and its mass determined by weighing the cup and subtracting the tare of the cup.

The bulk density was calculated as mass/untapped volume in $kg/m^3$.

The dry bulk density used was the measured bulk density of the biomass without addition of water.

The wet bulk density was the bulk density of the biomass with added water.

The ratio was calculated as wet bulk density divided by the dry bulk density.

The moisture content of the biomasses was determined by drying to constant weight.

After addition of water the moisture in the mixture was determined by calculation.

2.3 Results:

The results for 100% soya and 80% mixtures with soya are tabulated in the following:

| Soya | Maize | Wheat | Sun-flower | Rape seed | Fava bean | Pea | Water | Moisture In % | Bulk Density $kg/m^3$ | Ratio |
|---|---|---|---|---|---|---|---|---|---|---|
| 1000 g | | | | | | | 0 g | 10.9 | 665 | — |
| 1000 g | | | | | | | 100 g | 19.0 | 638 | 0.96 |
| 1000 g | | | | | | | 250 g | 28.7 | 500 | 0.75 |
| 1000 g | | | | | | | 450 g | 38.6 | 476 | 0.72 |
| 1000 g | | | | | | | 750 g | 49.1 | 470 | 0.71 |
| 1000 g | | | | | | | 900 g | 53.1 | 572 | 0.86 |
| 1000 g | | | | | | | 1100 g | 57.6 | 655 | 0.98 |
| 1000 g | | | | | | | 1400 g | 62.9 | 715 | 1.07 |
| 1000 g | | | | | | | 1900 g | 69.3 | 889 | 1.34 |
| 800 g | 200 g | | | | | | 0 g | 11.4 | 703 | — |
| 800 g | 200 g | | | | | | 450 g | 38.9 | 617 | 0.88 |
| 800 g | 200 g | | | | | | 900 g | 53.4 | 634 | 0.90 |
| 800 g | 200 g | | | | | | 1900 g | 69.4 | 1008 | 1.43 |
| 800 g | | 200 g | | | | | 0 g | 11.7 | 694 | — |
| 800 g | | 200 g | | | | | 450 g | 39.1 | 580 | 0.84 |
| 800 g | | 200 g | | | | | 900 g | 53.5 | 623 | 0.90 |
| 800 g | | 200 g | | | | | 1900 g | 69.5 | 960 | 1.38 |
| 800 g | | | 200 g | | | | 0 g | 10.4 | 683 | — |
| 800 g | | | 200 g | | | | 450 g | 38.2 | 554 | 0.81 |
| 800 g | | | 200 g | | | | 900 g | 52.9 | 598 | 0.88 |

-continued

| Soya | Maize | Wheat | Sun-flower | Rape seed | Fava bean | Pea | Water | Moisture In % | Bulk Density kg/m³ | Ratio |
|---|---|---|---|---|---|---|---|---|---|---|
| 800 g | | | 200 g | | | | 1900 g | 69.1 | 926 | 1.36 |
| 800 g | | | | 200 g | | | 0 g | 11.3 | 711 | — |
| 800 g | | | | 200 g | | | 100 g | 19.4 | 576 | 0.81 |
| 800 g | | | | 200 g | | | 250 g | 29.0 | 514 | 0.72 |
| 800 g | | | | 200 g | | | 450 g | 38.8 | 483 | 0.68 |
| 800 g | | | | 200 g | | | 750 g | 49.3 | 490 | 0.69 |
| 800 g | | | | 200 g | | | 900 g | 53.3 | 597 | 0.84 |
| 800 g | | | | 200 g | | | 1100 g | 57.8 | 528 | 0.74 |
| 800 g | | | | 200 g | | | 1900 g | 69.4 | 908 | 1.28 |
| 800 g | | | | | 200 g | | 0 g | 11.1 | 691 | — |
| 800 g | | | | | 200 g | | 450 g | 38.7 | 569 | 0.82 |
| 800 g | | | | | 200 g | | 900 g | 53.2 | 605 | 0.88 |
| 800 g | | | | | 200 g | | 1900 g | 69.3 | 941 | 1.36 |
| 800 g | | | | | | 200 g | 0 g | 11.2 | 703 | — |
| 800 g | | | | | | 200 g | 450 g | 38.7 | 488 | 0.69 |
| 800 g | | | | | | 200 g | 900 g | 53.2 | 728 | 1.04 |
| 800 g | | | | | | 200 g | 1900 g | 69.4 | 964 | 1.37 |

The results for 60% and 40% of soya mixtures with maize, sunflower and rapeseed as well as 100% rapeseed are tabulated in the following:

| Soya | Maize | Sun-flower | Rapeseed | Water | Moisture In % | Bulk Density kg/m³ | Ratio |
|---|---|---|---|---|---|---|---|
| 600 g | 400 g | | | 0 g | 11.8 | 703 | — |
| 600 g | 400 g | | | 250 g | 29.5 | 651 | 0.93 |
| 600 g | 400 g | | | 450 g | 39.2 | 626 | 0.89 |
| 600 g | 400 g | | | 750 g | 49.6 | 631 | 0.90 |
| 600 g | 400 g | | | 900 g | 53.6 | 666 | 0.95 |
| 600 g | 400 g | | | 1100 g | 58.0 | 723 | 1.03 |
| 600 g | 400 g | | | 1400 g | 63.3 | 796 | 1.13 |
| 600 g | | 400 g | | 0 g | 10.0 | 644 | — |
| 600 g | | 400 g | | 100 g | 18.2 | 530 | 0.82 |
| 600 g | | 400 g | | 250 g | 28.0 | 435 | 0.68 |
| 600 g | | 400 g | | 450 g | 37.9 | 433 | 0.67 |
| 600 g | | 400 g | | 750 g | 48.6 | 436 | 0.68 |
| 600 g | | 400 g | | 900 g | 52.6 | 480 | 0.75 |
| 600 g | | 400 g | | 1100 g | 57.1 | 449 | 0.70 |
| 600 g | | 400 g | | 1400 g | 62.5 | 616 | 0.96 |
| 600 g | | | 400 g | 0 g | 11.7 | 643 | — |
| 600 g | | | 400 g | 100 g | 19.7 | 560 | 0.82 |
| 600 g | | | 400 g | 250 g | 29.4 | 502 | 0.78 |
| 600 g | | | 400 g | 450 g | 39.1 | 503 | 0.78 |
| 600 g | | | 400 g | 750 g | 49.5 | 492 | 0.77 |
| 600 g | | | 400 g | 900 g | 53.5 | 516 | 0.80 |
| 600 g | | | 400 g | 1100 g | 57.9 | 545 | 0.85 |
| 600 g | | | 400 g | 1400 g | 63.2 | 655 | 1.02 |
| 400 g | 600 g | | | 0 g | 12.3 | 718 | — |
| 400 g | 600 g | | | 250 g | 29.9 | 636 | 0.89 |
| 400 g | 600 g | | | 450 g | 39.5 | 638 | 0.89 |
| 400 g | 600 g | | | 750 g | 49.9 | 666 | 0.93 |
| 400 g | 600 g | | | 900 g | 53.8 | 721 | 1.00 |
| 400 g | 600 g | | | 1100 g | 58.2 | 802 | 1.12 |
| 400 g | 600 g | | | 1400 g | 63.5 | 988 | 1.38 |
| 400 g | | 600 g | | 0 g | 9.5 | 654 | — |
| 400 g | | 600 g | | 100 g | 17.7 | 535 | 0.82 |
| 400 g | | 600 g | | 250 g | 27.6 | 422 | 0.65 |
| 400 g | | 600 g | | 450 g | 37.6 | 487 | 0.74 |
| 400 g | | 600 g | | 750 g | 48.3 | 491 | 0.75 |
| 400 g | | 600 g | | 900 g | 52.4 | 512 | 0.78 |
| 400 g | | 600 g | | 1100 g | 56.9 | 585 | 0.89 |
| 400 g | | 600 g | | 1400 g | 62.3 | 612 | 0.94 |
| 400 g | | | 600 g | 0 g | 12.1 | 658 | — |
| 400 g | | | 600 g | 100 g | 20.1 | 556 | 0.84 |
| 400 g | | | 600 g | 250 g | 29.7 | 471 | 0.72 |
| 400 g | | | 600 g | 450 g | 39.4 | 458 | 0.70 |
| 400 g | | | 600 g | 750 g | 49.8 | 486 | 0.74 |
| 400 g | | | 600 g | 900 g | 53.7 | 486 | 0.74 |
| 400 g | | | 600 g | 1100 g | 58.1 | 531 | 0.81 |
| 400 g | | | 600 g | 1400 g | 63.4 | 605 | 0.92 |
| 0 g | 1000 g | | | 0 g | 12.9 | 616 | — |
| 0 g | | 1000 g | | 100 g | 20.8 | 484 | 0.79 |
| 0 g | | 1000 g | | 250 g | 30.3 | 438 | 0.71 |
| 0 g | | 1000 g | | 450 g | 39.9 | 457 | 0.74 |
| 0 g | | 1000 g | | 750 g | 50.2 | 507 | 0.82 |
| 0 g | | 1000 g | | 900 g | 54.1 | 535 | 0.87 |
| 0 g | | 1000 g | | 1100 g | 58.5 | 585 | 0.95 |
| 0 g | | 1000 g | | 1400 g | 63.7 | 688 | 1.12 |

Figure 3:
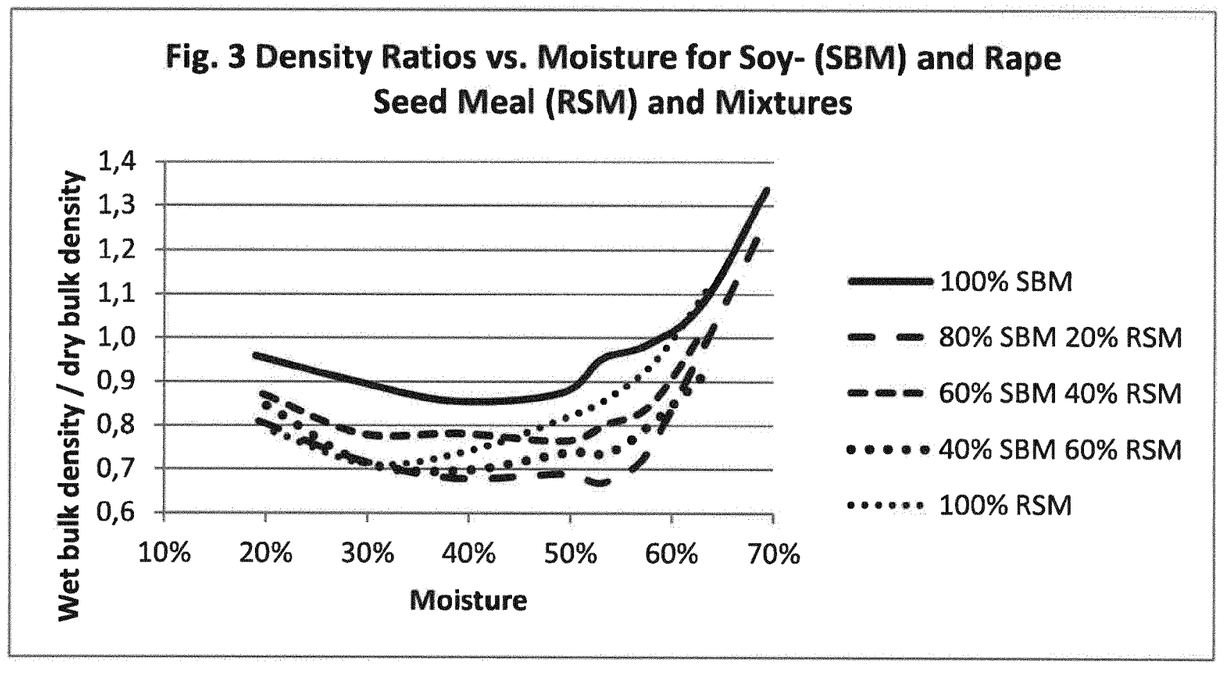
FIG. 3 shows the density ratios (wet bulk density/dry bulk density) vs. moisture for soya- and rape seed meal and their mixtures.

The density ratios (wet bulk density/dry bulk density) vs. moisture for soya- and rape seed meal and their mixtures are shown graphically in FIG. 3.

Example 3

Lab-scale incubation tests of prior art method vs. new technology method 3.1 Background:

The background for the following lab-scale incubation tests was to imitate the conditions for the prior art method (PAM) as described in WO 2013050456 and the conditions in the method of the present invention (NTM).

In the prior art method (PAM) the developed $CO_2$ has free access to be released to the surroundings, whereas this is more limited in the new technology method (NTM) of the present invention i.e. the partial $CO_2$ pressure is higher.

3.2 Materials and Methods:

3.2.1—Materials

Biomasses: Soya Bean Meal (SBM), Rape Seed Meal (RSM) and Sunflower Seed Meal (SSM)—as described in section 2.1.

Water: Normal tap water

Yeast: Baker's yeast from De Danske Grfabrikker, Grenå, DK

Processing aid: α-galactosidase from Bio-Cat (12,500 U/g)

Each incubation mixture had a biomass content of 150 g of DM, varying amount of water, 0.4% yeast by weight of DM of biomass and 0.12% α-galactosidase by weight of DM of biomass.

The compositions of the incubation mixtures are tabulated in the following:

| Biomass | Moisture in % by weight | SBM 90.1% DM (g) | RSM 87.2% DM (g) | SSM 90.7% DM (g) | Water (mL) | Yeast (20% DM) (mL) | α-galactosidase (mg) |
|---|---|---|---|---|---|---|---|
| 100% SBM | 45 | 166.7 | — | — | 103 | 3.0 | 182 |
| 100% SBM | 60 | 166.7 | — | — | 205 | 3.0 | 182 |
| 100% SBM | 65 | 166.7 | — | — | 259 | 3.0 | 182 |
| 80% SBM/ 20% RSM | 45 | 133.3 | 34.4 | — | 102 | 3.0 | 182 |
| 80% SBM/ 20% RSM | 60 | 133.3 | 34.4 | — | 204 | 3.0 | 182 |
| 60% SBM/ 40% SSM | 45 | 100 | — | 66.2 | 104 | 3.0 | 182 |
| 60% SBM/ 40% SSM | 60 | 100 | — | 66.2 | 206 | 3.0 | 182 |

3.2.2—Experimental Method Used

Incubation Tank:

For the PAM-method conical flasks half-filled and loosely closed with aluminium foil were used. For the NTM-method strong plastic bags, squeezed by hand to remove air and closed with a strap so that $CO_2$ could escape were used.

Incubation:

All samples were incubated for 16 hours at 32° C. in a thermostated water bath. The incubation was stopped by heating to 100° C. for 30 minutes, except for the samples for ethanol analyses where the incubation was stopped by freezing.

Analytical Methods:

The analytical methods used are referred under the following individual results.

3.3 Results:

3.3.1—Density

The determination of bulk density was performed by pouring an amount of material (250-460 mL) in a 500 mL graduated cylinder and reading the volume after levelling the surface by gently shaking (not tapping) the cylinder. Following this, the weight of the material was determined.

The calculations were done as described in section 2.2.

The results are tabulated in the following:

| Method | Biomass | Moisture in % by weight | Density ratio | Dry bulk density-substrate $kg/m^3$ | Wet bulk density-substrate $kg/m^3$ (1) | Wet bulk density-After incubation $kg/m^3$ (2) | Δ Wet bulk density $kg/m^3$ (2) minus (1) |
|---|---|---|---|---|---|---|---|
| PAM | 100% SBM | 45 | 0.89 | 654 | 583 | 568 | −15 |
|  | 100% SBM | 60 | 1.05 | 642 | 673 | 645 | −28 |
|  | 100% SBM | 65 | 1.29 | 654 | 843 | 552 | −291 |
| NTM | 100% SBM | 45 | 0.90 | 641 | 580 | 926 | 346 |
|  | 100% SBM | 60 | 1.06 | 641 | 682 | 852 | 170 |
|  | 100% SBM | 65 | 1.27 | 641 | 817 | 992 | 175 |
| PAM | 80% SBM/ 20% RSM | 45 | 0.89 | 671 | 598 | 530 | −68 |
|  | 80% SBM/ 20% RSM | 60 | 1.05 | 671 | 701 | 635 | −66 |
| NTM | 80% SBM/ 20% RSM | 45 | 0.90 | 641 | 580 | 869 | 289 |
|  | 80% SBM/ 20% RSM | 60 | 1.11 | 658 | 732 | 970 | 238 |
| PAM | 60% SBM/ 40% SSM | 45 | 0.82 | 652 | 536 | 506 | −30 |
|  | 60% SBM/ 40% SSM | 60 | 1.06 | 665 | 703 | 518 | −185 |
| NTM | 60% SBM/ 40% SSM | 45 | 0.84 | 639 | 535 | 858 | 323 |
|  | 60% SBM/ 40% SSM | 60 | 1.06 | 652 | 692 | 1045 | 353 |

Comments:

From the results, it is noticed that after the incubation by the PAM-method the bulk density is reduced and with the NTM-method the density is increased.

To test the influence of squeezing the bags, four different substrates were treated without incubation. The results for the four measurements were a maximum increase of 60 kg/m$^3$ and a mean value of 33.5 kg/m$^3$. Consequently, the density increase is an obvious fact.

3.3.2 Protein Content

The crude protein content was determined according to the Dumas method, using 6.25 as conversion factor.

The results are tabulated in the following:

| Method | Biomass | Moisture in % by weight | Protein content in the biomass In % by weight of DM (1) | Protein content in the transformation product In % by weight of DM (2) | Δ Protein content In % by weight of DM (2) minus (1) | Protein content Increase in % relative |
|---|---|---|---|---|---|---|
| PAM | 100% SBM | 45 | 54.8 | 60.4 | 5.6 | 10.2 |
|  | 100% SBM | 60 | 54.8 | 61.6 | 6.8 | 12.4 |
|  | 100% SBM | 65 | 54.8 | 62.1 | 7.3 | 13.3 |
| NTM | 100% SBM | 45 | 54.8 | 59.9 | 5.1 | 9.3 |
|  | 100% SBM | 60 | 54.8 | 60.8 | 6.0 | 10.9 |
|  | 100% SBM | 65 | 54.8 | 61.7 | 6.9 | 12.6 |
| PAM | 80% SBM/20% RSM | 45 | 52.6 | 56.0 | 3.4 | 6.4 |
|  | 80% SBM/20% RSM | 60 | 52.6 | 58.3 | 5.7 | 10.8 |
| NTM | 80% SBM/20% RSM | 45 | 52.6 | 56.6 | 4.0 | 7.6 |
|  | 80% SBM/20% RSM | 60 | 52.6 | 57.3 | 4.7 | 8.9 |
| PAM | 60% SBM/40% SSM | 45 | 48.9 | 51.7 | 2.8 | 5.7 |
|  | 60% SBM/40% SSM | 60 | 48.9 | 54.3 | 5.4 | 11.0 |
| NTM | 60% SBM/40% SSM | 45 | 48.9 | 54.1 | 5.2 | 10.6 |
|  | 60% SBM/40% SSM | 60 | 48.9 | 52.0 | 3.1 | 6.3 |

3.3.3 Alcohol Content in Incubated Mixture

The ethanol content was analyzed by Eurofins according to their method with internal code—RTTEF.

The results are tabulated in the following:

| Method | Biomass group | Moisture in % by weight | EtOH content in gram per kg wet weight of incubated mixture | EtOH content in gram per kg dry weight of incubated mixture | Ranking Within biomass group |
|---|---|---|---|---|---|
| PAM | 100% SBM | 45 | 12.0 | 21.8 | 6 |
|  | 100% SBM | 60 | 20.0 | 50.0 | 3 |
|  | 100% SBM | 65 | 13.0 | 48.6 | 4 |
| NTM | 100% SBM | 45 | 18.0 | 32.7 | 5 |
|  | 100% SBM | 60 | 21.0 | 52.6 | 1 |
|  | 100% SBM | 65 | 18.0 | 51.4 | 2 |
| PAM | 80% SBM/20% RSM | 45 | 19.0 | 34.5 | 3 |
|  | 80% SBM/20% RSM | 60 | 13.0 | 32.5 | 4 |
| NTM | 80% SBM/20% RSM | 45 | 23.0 | 41.8 | 2 |
|  | 80% SBM/20% RSM | 60 | 20.5 | 51.3 | 1 |

-continued

| Method | Biomass group | Moisture in % by weight | EtOH content in gram per kg wet weight of incubated mixture | EtOH content in gram per kg dry weight of incubated mixture | Ranking Within biomass group |
|---|---|---|---|---|---|
| PAM | 60% SBM/ 40% SSM | 45 | 20.0 | 36.4 | 2 |
|  | 60% SBM/ 40% SSM | 60 | 13.0 | 32.5 | 4 |
| NTM | 60% SBM/ 40% SSM | 45 | 18.0 | 32.7 | 3 |
|  | 60% SBM/ 40% SSM | 60 | 18.0 | 45.0 | 1 |

Comments:

From the ranking of the EtOH formed within biomass group, it is shown that the NTM-method results in more alcohol detected than the PAM-method does.

3.3.4 Oligosaccharides

The content of stachyose and raffinose was determined by thin-layer chromatography. Stationary phase—Silica gel 60 (Merck 1.05553.0001)

Mobile phase—120 mL n-butanol, 80 mL pyridine, and 60 mL demineralized water Spots are visualized with a liquid composed of 8 g diphenylamine, 335 mL acetone, 8 mL aniline, and 60 mL phosphoric acid.

Sugar concentrations were determined by comparison with known standards.

The results are tabulated in the following:

| Method | Biomass | Moisture In % by weight DM | Stachyose In biomass In % by weight DM | Raffinose In biomass In % by weight DM | Stachyose + Raffinose In biomass In % by weight DM | Stachyose After incubation In % by weight DM | Raffinose After incubation In % by weight DM | Stachyose + Raffinose After incubation In % by weight DM | Reduction in % relative |
|---|---|---|---|---|---|---|---|---|---|
| PAM | 100% SBM | 45 | 4.7 | 1.0 | 5.7 | 0.2 | 0.2 | 0.4 | 93 |
|  | 100% SBM | 60 | 4.7 | 1.0 | 5.7 | 0 | 0 | 0 | 100 |
|  | 100% SBM | 65 | 4.7 | 1.0 | 5.7 | 0 | 0 | 0 | 100 |
| NTM | 100% SBM | 45 | 4.7 | 1.0 | 5.7 | 0.2 | 0.2 | 0.4 | 93 |
|  | 100% SBM | 60 | 4.7 | 1.0 | 5.7 | 0 | 0 | 0 | 100 |
|  | 100% SBM | 65 | 4.7 | 1.0 | 5.7 | 0 | 0 | 0 | 100 |
| PAM | 80% SBM/ 20% RSM | 45 | 4.0 | 0.9 | 4.9 | 0.2 | 0.2 | 0.4 | 92 |
|  | 80% SBM/ 20% RSM | 60 | 4.0 | 0.9 | 4.9 | 0 | 0 | 0 | 100 |
| NTM | 80% SBM/ 20% RSM | 45 | 4.0 | 0.9 | 4.9 | 0.2 | 0.2 | 0.4 | 92 |
|  | 80% SBM/ 20% SBM | 60 | 4.0 | 0.9 | 4.9 | 0 | 0 | 0 | 100 |
| PAM | 60% SBM/ 40% SSM | 45 | 2.9 | 1.2 | 4.1 | 0.2 | 0.2 | 0.4 | 90 |
|  | 60% SBM/ 40% SSM | 60 | 2.9 | 1.2 | 4.1 | 0 | 0 | 0 | 100 |
| NTM | 60% SBM/ 40% SSM | 45 | 2.9 | 1.2 | 4.1 | 0.2 | 0.2 | 0.4 | 90 |
|  | 60% SBM/ 40% SSM | 60 | 2.9 | 1.2 | 4.1 | 0 | 0 | 0 | 100 |

Comments:

The two methods performed equally well, and at a moisture content higher than 45% the reduction of the oligosaccharides measured was 100%.

3.3.5 Organic Acids

The contents of succinic- and acetic acids were analyzed by Eurofins according to their method with internal code—HEG12.

The results are tabulated in the following:

| Method | Biomass group | Moisture in % by weight | Succinic acid in mg per kg DM | Acetic acid in mg per kg DM | Succinic + Acetic acid in mg per kg DM | Ranking Within biomass group |
|---|---|---|---|---|---|---|
| PAM | 100% SBM | 45 | 1818 | 3091 | 4909 | 3 |
|  | 100% SBM | 60 | 4500 | 1625 | 6125 | 1 |
|  | 100% SBM | 65 | 1314 | 1114 | 2428 | 5 |
| NTM | 100% SBM | 45 | 600 | 1818 | 2418 | 6 |
|  | 100% SBM | 60 | 1300 | 1150 | 2450 | 4 |
|  | 100% SBM | 65 | 4000 | 1371 | 5371 | 2 |
| PAM | 80% SBM/ 20% RSM | 45 | 3636 | 3636 | 7272 | 1 |
|  | 80% SBM/ 20% RSM | 60 | 4250 | 1750 | 6000 | 2 |
| NTM | 80% SBM/ 20% RSM | 45 | 1818 | 1437 | 3255 | 3 |
|  | 80% SBM/ 20% RSM | 60 | 1925 | 925 | 2850 | 4 |
| PAM | 60% SBM/ 40% SSM | 45 | 5091 | 1527 | 6618 | 1 |
|  | 60% SBM/ 40% SSM | 60 | 5000 | 600 | 5600 | 2 |
| NTM | 60% SBM/ 40% SSM | 45 | 2545 | 636 | 3181 | 3 |
|  | 60% SBM/ 40% SSM | 60 | 2500 | 325 | 2825 | 4 |

Comments:

From the ranking within biomass group, it is shown that the PAM-method produces more succinic and acetic acid than the NTM-method does.

3.4 Conclusions:

On the basis of the obtained results it can be seen that the NTM-method produces a solid transformation product with slightly less protein and less succinic and acetic acid than the product based on the PAM-method. At the same time the alcohol content in the incubation mixture resulting from the NTM-method is higher.

Example 4

Incubation in a Continuous Vertical Incubator of a Biomass Comprising Polysaccharides and Proteins from Pulses In the following the incubation in a vertical, closed and non-stirred incubator of a biomass based on defatted soya is illustrated.

4.1 Incubation Mixture:

A mixture of dehulled, defatted and desolventised soya flakes and a slurry of yeast and water was prepared continuously in amounts to reach a dry matter content of 45% by weight in the mixture.

The incubation mixture had a content of 3.5% by weight of yeast based on total dry matter. The ratio wet bulk density/dry bulk density of the incubation mixture was 0.895.

4.2 Incubator:

The pilot incubator used was an insulated, cylindrical oblong stainless-steel tube with an internal diameter of 1.55 m and a total height of 4.75 m. In the upper part, there was an array of three rotating paddle type level monitors to regulate the inlet and distribution system to a level at 4.25 m. This gives the incubator an effective operating volume of 8 $m^3$.

Furthermore, the incubator was equipped with a temperature probe at the inlet as well as at the outlet.

4.3 Test Procedure:

The incubator was filled with incubation mixture at the rate of 1000 litre per hour. After eight hours the incubator was filled to operating level and the outlet means were set at a rate to keep the level of filling constant.

An aliquot volume of approx. 30 litres was taken after 10 hours of the test run and incubated at 100° C. with live steam for 25 min. and the surplus steam comprising crude ethanol was transferred to a cooling heat exchanger.

Subsequently, the wet solid transformation product of the biomass was flash dried and milled.

The overall incubation parameters were the following:
Incubation time—8 hours
Inlet temperature—25.2° C.
Outlet temperature—32.3° C.

4.4 Results:

The separated crude ethanol content corresponded to a yield of 4.7 kg per 100 kg of biomass. The solid transformation product of the biomass had a total crude protein (N×6.25) content of 58.3%. The water content of the dried product was 5.4% by weight.

Furthermore, anti-nutritional factors in the dried, solid transformation product were significantly reduced:

| Parameter | Biomass | Solid transformation product |
|---|---|---|
| Oligosaccharides | 10.2% | 0.5% |
| Trypsin inhibitor | 43,000 TIU/g | 1,900 TIU/g |
| B-conglycinin | 130,000 ppm | 2 ppm |

The solid transformation product is highly nutritious and palatable and thus suitable as an ingredient in a number of food and feed products or nutritional supplements. Furthermore, it can be used as an excipient in pharma products and in cosmetics e.g. bath formulations.

Example 5

Incubation in a Continuous Vertical Incubator of a Biomass Comprising Polysaccharides and Proteins from a Mixture of Pulses and Cereals In the following the incubation in a vertical, closed and non-stirred incubator of a biomass based on a mixture of defatted soya and wheat is illustrated.

5.1 Incubation Mixture:

A mixture containing 10% by weight of dry matter of crushed wheat and 90% by weight of dry matter of dehulled, defatted and desolventised soya flakes and a slurry of yeast, enzymes and water was prepared continuously in amounts to reach a dry matter content of 40% by weight in the mixture. The incubation mixture had a content of 3% by weight of yeast based on total dry matter and 0.4% by weight based on dry matter of wheat of Viscozyme Wheat, Spirizyme Fuel and Liquozyme all from Novozymes.

The ratio wet bulk density/dry bulk density of the incubation mixture was 0.984.

5.2 Incubator:

The incubator was as described in example 4.

5.3 Test Procedure:

The test procedure was as described in example 4 except that in this process the inlet means was set to run at a volume speed of 500 liters/h.

The overall incubation parameters were the following:
Incubation time—16 hours
Inlet temperature—25.1° C.
Outlet temperature—33.1° C.

5.4 Results:

The separated crude ethanol content corresponded to a yield of 8.4 kg per 100 kg of biomass. The solid transformation product of the biomass had a crude protein content (N×6.25) of 59.4% and a water content of 6.2% by weight.

The invention claimed is:

1. A method for the simultaneous production of a solid transformation product of a biomass substrate and crude ethanol, comprising:
preparing a substrate from a milled or flaked biomass comprising proteinaceous matter which originates from one or more of soya bean, rape seed, and mixtures thereof;
mixing said substrate with live yeast in a dry matter ratio of from 1:1 to 10,000:1 and adding water in an amount which provides a water content of from 35% to 70% by weight, and a ratio of wet bulk density to dry bulk density of from 0.60 to 1.45 in the resulting mixture;
incubating said mixture for 1-48 hours at a temperature of 20-60° C.; and
separating crude ethanol and wet solid transformation product from said mixture;
wherein said incubating is performed as a continuous plug-flow process in a vertical, non-agitated, closed incubation tank wherein transport of the biomass is mediated by gravitational force, with an inlet for said mixture and additives and an outlet for said solid transformation product and crude ethanol.

2. A method according to claim 1, wherein at least 20% by weight of said biomass comprises proteinaceous matter originating from defatted soya flakes.

3. A method according to claim 1, wherein at least 20% by weight of said biomass comprises proteinaceous matter originating from defatted rape seeds.

4. A method according to claim 1, wherein at least 60% by weight of said biomass comprises proteinaceous matter originating from defatted soya flakes.

5. A method according to claim 1, wherein at least 60% by weight of said biomass comprises proteinaceous matter originating from defatted rape seed.

6. A method according to claim 1, wherein said biomass further comprises one or more of oligosaccharides, polysaccharides, and oils and/or fats from seeds of oil-bearing plants.

7. A method according to claim 1, wherein said solid transformation product is a product of the transformation of proteinaceous matter, oligosaccharides, and/or polysaccharides originating from said biomass.

8. A method according to claim 1, wherein the dry matter ratio of biomass to yeast is from 2:1 to 5000:1.

9. A method according to claim 1, wherein water is added to said substrate in an amount to provide a ratio of wet bulk density to dry bulk density of from 0.65 to 1.40 in the substrate.

10. A method according to claim 1, wherein said yeast is selected from *Saccharomyces cerevisiae* strains of spent brewer's yeast, spent distiller's yeast, baker's yeast, spent yeast from wine production, and yeast strains fermenting C5 sugars.

11. A method according to claim 1, further comprising adding one or more processing aids selected from enzymes, plant components, and organic and inorganic processing agents to the substrate or mixture before or during said incubating.

12. A method according to claim 1, comprising keeping the filling degree of said closed incubation tank constant.

13. A method according to claim 1, further comprising adding α-galactosidase to the substrate or mixture before or during said incubating.

14. A method according to claim 13, wherein the α-galactosidase is added as an α-galactosidase preparation having an activity of about 5,000 α-galactosidase units/g, and is added to the substrate or mixture in an amount of from about 0.001% to about 1% by weight of the dry matter of the substrate or mixture.

15. A method according to claim 1, wherein said incubating is carried out under anaerobic conditions.

16. A method according to claim 1, wherein the water content in said mixture is from 40% to 70% by weight.

17. A method according to claim 1, further comprising drying the solid transformation product.

18. A method according to claim 17, further comprising milling the dried solid transformation product.

19. A method according to claim 1, where said non-agitated, closed incubation tank is of a vertical, oblong cylindrical, or polyhedral type.

20. A method according to claim 1, wherein said non-agitated, closed incubation tank has a conical shape wherein an upper region has a smaller diameter than a lower region.

21. A method according to claim 1, wherein said non-agitated, closed incubation tank is provided with insulating matting or a thermal dimple jacket.

22. A method according to claim 1, wherein at least 90% of crude ethanol produced is recovered.

23. A method according to claim 1, wherein the solid transformation product comprises proteins in an amount of 25-90% by weight on dry matter basis.

24. A method according to claim 23, further comprising drying the solid transformation product to a water content of not more than 15%.

25. A method according to claim 1, wherein the solid transformation product comprises at least 40% proteinaceous matter originating from soya.

26. A method according to claim 1, wherein the solid transformation product comprises at least 40% proteinaceous matter originating from rape seed.

27. A method according to claim 1, wherein the solid transformation product comprises proteins originating from plant parts of soya, rape seed, or sun flower, or mixtures thereof in an amount of from 30% to 65% by weight on dry matter basis.

28. A method according to claim 1, wherein the solid transformation product comprises a total amount of raffinose and stachyose of 3% by weight or less.

29. A method according to claim 1, wherein the solid transformation product comprises organic acids selected from succinic acid, acetic acid, and mixtures thereof in amounts of from 0.01% to 0.5% by weight.

30. A method according to claim 1, wherein the biomass further comprises proteinaceous matter originating from fava beans, peas, sunflower seeds, lupine, cereals, and/or grasses.

31. A method according to claim 1, wherein the solid transformation product comprises proteins in an amount of 25-90% by weight on dry matter basis, and glyceride in an amount of 0.05-30% by weight on dry matter basis.

* * * * *